(12) United States Patent
Willis

(10) Patent No.: US 7,275,547 B2
(45) Date of Patent: Oct. 2, 2007

(54) METHOD AND SYSTEM FOR DETERMINING THE LOCATION OF A MEDICAL PROBE USING A REFERENCE TRANSDUCER ARRAY

(75) Inventor: Parker Willis, Atherton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 701 days.

(21) Appl. No.: 10/682,627

(22) Filed: Oct. 8, 2003

(65) Prior Publication Data

US 2005/0080334 A1    Apr. 14, 2005

(51) Int. Cl.
*A61B 19/00* (2006.01)
*A61B 8/12* (2006.01)
*A61N 19/00* (2006.01)

(52) U.S. Cl. .................. 128/899; 600/439; 607/122

(58) Field of Classification Search ............... 128/899; 600/407, 409–410, 417, 423–424, 427, 429, 600/437–471; 607/115–116, 119–131
See application file for complete search history.

(56) References Cited

U.S. PATENT DOCUMENTS

| | | | | |
|---|---|---|---|---|
| 3,750,152 A | * | 7/1973 | Waful ......................... | 367/100 |
| 4,407,294 A | * | 10/1983 | Vilkomerson ............... | 600/461 |
| 4,459,851 A | * | 7/1984 | Crostack ..................... | 73/587 |
| 4,559,621 A | | 12/1985 | Delignieres | |
| 4,805,622 A | * | 2/1989 | Riedlinger et al. ......... | 600/442 |
| 4,913,157 A | * | 4/1990 | Pratt et al. .................. | 600/449 |
| 5,042,486 A | * | 8/1991 | Pfeiler et al. ............... | 600/424 |
| 5,383,874 A | | 1/1995 | Jackson et al. | |
| 5,443,489 A | | 8/1995 | Ben-Haim | |
| 5,485,849 A | | 1/1996 | Panescu et al. | |

(Continued)

FOREIGN PATENT DOCUMENTS

WO    WO99/58055    11/1999

OTHER PUBLICATIONS

PCT International Search Report for PCT/US2004/031476, Applicant: Scimed Life Systems, Inc., Forms PCT/ISA/210 and 220, dated Jan. 31, 2005 (7 pages).

(Continued)

*Primary Examiner*—Francis J. Jaworski
(74) *Attorney, Agent, or Firm*—Vista IP Law Group LLP

(57) ABSTRACT

The present invention provides systems and methods for determining the coordinates of a location element mounted on a medical probe. First and second signals are transmitted between the location element and a first and second reference transducers, which may be arranged in a reference array that can be attached to a patient's skin. A transit time difference between the first and second signals is determined, e.g., using a thresholding or correlation technique. A distance difference between a first distance extending from the location element to the first reference element and a second distance extending from the location element to the second reference element is then determined based on the transit time difference. An angle between the reference array and the location element can then be determined based on the determined distance difference and a known distance between the first and second reference transducers. The coordinates of the location element within a coordinate system are then determined based on the determined angle and the distance between the transducer array and the location element.

67 Claims, 9 Drawing Sheets

U.S. PATENT DOCUMENTS

| | | |
|---|---|---|
| 5,494,042 A | 2/1996 | Panescu et al. |
| 5,515,853 A | 5/1996 | Smith et al. |
| 5,724,978 A * | 3/1998 | Tenhoff ................ 600/467 |
| 5,779,638 A * | 7/1998 | Vesely et al. ............ 600/437 |
| 5,797,849 A * | 8/1998 | Vesely et al. ............ 600/461 |
| 5,833,621 A | 11/1998 | Panescu et al. |
| 5,860,926 A | 1/1999 | Barabash et al. |
| 5,868,673 A | 2/1999 | Vesely |
| 5,899,863 A | 5/1999 | Hatfield et al. |
| 5,954,653 A | 9/1999 | Hatfield et al. |
| 6,019,725 A | 2/2000 | Vesely et al. |
| 6,032,066 A * | 2/2000 | Lu et al. ................. 600/407 |
| 6,101,409 A | 8/2000 | Swanson et al. |
| 6,102,861 A | 8/2000 | Avila et al. |
| 6,138,513 A | 10/2000 | Barabash et al. |
| 6,216,027 B1 * | 4/2001 | Willis et al. ............. 600/424 |
| 6,226,546 B1 | 5/2001 | Evans |
| 6,230,042 B1 * | 5/2001 | Slettenmark ............ 600/424 |
| 6,298,261 B1 * | 10/2001 | Rex ........................ 600/424 |
| 6,352,510 B1 | 3/2002 | Barabash et al. |
| 6,353,751 B1 | 3/2002 | Swanson et al. |
| 6,457,365 B1 | 10/2002 | Stephens et al. |
| 6,464,638 B1 | 10/2002 | Adams et al. |
| 6,490,474 B1 | 12/2002 | Willis et al. |
| 6,494,837 B2 | 12/2002 | Kim et al. |
| 6,537,220 B1 | 3/2003 | Friemel et al. |
| 6,546,271 B1 | 4/2003 | Reisfeld |
| 6,551,246 B1 | 4/2003 | Ustuner et al. |
| 6,569,104 B2 | 5/2003 | Ono et al. |
| 6,822,570 B2 * | 11/2004 | Dimmer et al. .......... 340/572.1 |
| 6,950,689 B1 | 9/2005 | Willis et al. |

OTHER PUBLICATIONS

PCT Written Opinion of the International Search Authority for PCT/US2004/031476, Applicant: Scimed Life Systems, Inc., Form PCT/ISA/237, dated Jan. 31, 2005 (6 pages).

* cited by examiner

METHOD AND SYSTEM FOR DETERMINING THE LOCATION OF A MEDICAL PROBE USING A REFERENCE TRANSDUCER ARRAY

FIELD OF THE INVENTION

The present inventions generally relate to medical probes, and more particularly to systems and methods for determining the location of a medical probe.

BACKGROUND OF THE INVENTION

It is often necessary or desirable to determine the location of a medical probe when performing a diagnostic and/or therapeutic procedure on a patient. As one example, catheters, whether intravascular or extravascular, must typically be navigated through a patient's body in order to locate the operative portion of the catheter adjacent a target tissue region. Traditionally, this has been accomplished using fluoroscopy. In this case, radiopaque elements are located on the distal end of the catheter and fluoroscopically imaged as the catheter is routed through the body. As a result, a two-dimensional image of the catheter, as represented by the illuminated radiopaque elements, thereby allowing the physician to roughly determine the location of the catheter. The use of fluoroscopy in locating catheters is somewhat limited, however, in that the physician is only able to visualize the catheter and surrounding tissues in two dimensions. In addition, fluoroscopy does not image soft tissues, making it difficult for the physician to visualize features of the anatomy as a reference for the navigation. In many procedures, such as cardiac electrophysiology therapy, however, identification of the target tissue region and/or catheter navigation must be made with reference to such features, e.g., the ostium of a pulmonary vein. In this case, fluoroscopy is only used to introduce the catheter within the organ containing the target tissue, e.g., within the heart, and the catheter must be navigated within the heart using other means.

Various types of systems have been developed, or at least conceived, to address this issue. Many of these systems have been focused on the need to efficiently and accurately provide electrophysiological therapy to heart tissue in order to treat cardiac rhythm disturbances. During these procedures, a physician steers a mapping/ablation catheter through a main vein or artery into the interior region of the heart that is to be treated, e.g., using fluoroscopy. The physician makes an electrical map of the interior region of the heart in order to determine the source of the cardiac rhythm disturbances, i.e., the targeted cardiac tissue. The physician then places an ablating element carried on the catheter near the targeted cardiac tissue, and directs energy from the ablating element to ablate the tissue and form a lesion, thereby treating the cardiac disturbance.

Recent advancements in transducer and processing technology have enabled commercially available real-time three-dimensional acoustic imaging of the heart and surrounding vasculature. For example, the SONOS 7500 imaging system, marketed by Philips Medical System located in Bothell, Wash., is an example of one such commercially available system that uses an external device to generate the image. This system provides real-time three-dimensional images of cardiac structures with resolution that is adequate for assisting in catheter navigation and placement during electrophysiology procedures. See, e.g., Lang et al., "A Fantastic Journey: 3D Cardiac Acoustic Goes Live," Radiology Management, November/December 2002; and "Phillips Prepares to Launch System Upgrade Capable of True Real-Time 3D Echo," Diagnostic Imaging Scan, The Global Biweekly of Medical Imaging, Vol. 16, No. 18, Sep. 11, 2002, the disclosures of which are hereby expressly incorporated herein by reference.

Although real-time three-dimensional imaging systems, such as the SONOS 7500, provide high resolution images, these types of imaging systems are somewhat limited in the field of electrophysiology therapy, because they do not correlate catheter positions and internal anatomical structures with previously recorded signals and ablation locations.

U.S. Pat. No. 6,353,751 describes a system that can be used to navigate a catheter relative to previously recorded signals and ablation locations. The system includes a basket assembly of mapping electrodes that can be deployed within a chamber of a heart. Once deployed, the basket electrodes can be used to map the heart in order to identify and locate the tissue region to be therapeutically treated, e.g., by identifying the specific basket electrode that is adjacent the tissue region. An ablation catheter can then be introduced into the heart chamber and navigated relative to the basket by wirelessly transmitting electrical signals between the electrodes on the basket assembly and a positioning electrode located on the distal end of a catheter. An ablation electrode on the catheter, which may be the same as the positioning electrode, can then be navigated relative to the basket electrodes, and thus, placed adjacent the target tissue region and operated to create a lesion.

In another navigation system, commercially available as the Realtime Position Management™ (RPM) tracking system and developed by Boston Scientific Corporation, located in San Jose, Calif., a graphical representation of a catheter is displayed in a three-dimensional computer-generated representation of a body tissue, e.g., heart chamber. The three-dimensional representation of the body tissue is produced by mapping the geometry of the inner surface of the body tissue in a three-dimensional coordinate system by placing plurality of acoustic location transducers on an ablation/mapping catheter, and moving the catheter to multiple points on the body tissue while tracking the positions of the catheter within the coordinate system using the location transducers. A graphical anatomical shell is then deformed to conform to the transducer positions as they are acquired. The positions of other catheters to be guided within the body, e.g., a mapping/ablation catheter, is determined by placing acoustic transducers on the these catheters and tracking the positions of the catheters within the three-dimensional coordinate system.

The three-dimensional coordinate system is internally established in the RPM system by placing two reference catheters within known locations of the heart, such as the coronary sinus or right ventricular apex, and transmitting between acoustic transducers located on the reference catheters. The location of the ablation/mapping electrode can then be determined by triangulating each of the location transducers relative to the reference transducers.

U.S. Pat. No. 5,868,673 discloses another means for navigating an ablation probe with tissue in order to facilitate treatment of tumors. In this system, reference acoustic transducers are affixed to the exterior of the patient in order to establish an external three-dimensional coordinate system for locating a location transducer located on the ablation probe as it is moved within the tissue.

In order to provide a less invasive and time-consuming electrophysiological procedure, it may be desirable use a system similar to that described in U.S. Pat. No. 5,868,673, in order to establish an external three-dimensional coordinate system. For example, acoustic reference transducers can be affixed to regions of the patient's body in a manner that allows communication between these reference transducers and location transducers on an ablation/mapping catheter. In this manner, no reference catheters need be introduced into the patient's body, thereby lessening the time of the electrophysiological procedure and any discomfort experienced by the patient.

Unfortunately, the availability of acoustic windows through the patient's chest needed to provide communication channels between the spaced-apart reference transducers and the location transducers located within the heart are somewhat limited. Specifically, anatomical regions, such as the ribs and lungs, have vastly different acoustic characteristics than the surrounding tissue. Thus, as the acoustic energy passes through the patient's body, a majority of the energy will reflect backwards at the interface between the surrounding tissue and the ribs and lungs. Even if a transducer does receive a portion of the acoustic signal that passes through the interface, the velocity of the acoustic signal through the ribs and lungs will be different from the velocity of the acoustic signal through the surrounding tissue. As a result, errors will be injected into the navigation algorithm, which assumes a constant acoustic velocity through soft tissue—about the same acoustic velocity as through water.

SUMMARY OF THE INVENTION

In accordance with a first aspect of the present invention, a method of determining the location of a medical probe is provided. The method comprises wirelessly transmitting first and second signals (e.g., acoustic signals) between a location element mounted on the medical probe and first and second reference elements. In the preferred method, the first and second reference elements are located on the exterior of a patient, and are arranged in a manner that allows the internal location element to communicate with the first and second reference elements through a single acoustic window within the patient's body. For example, the first and second elements can be arranged as a tightly spaced array.

The first and second signals can be transmitted in a variety of manners. For example, the first and second signals can be transmitted from the location element to the respective first and second reference elements. In this case, the first and second signals are preferably simultaneously transmitted, e.g., in response to a single electrical pulse, which results in the transmission of first and second signals to the respective first and second reference elements. The first and second signals can also be transmitted from the respective first and second elements to the location element. In this case, the first and second signals are preferably transmitted at different times.

The method further comprises determining a transit time difference between the first and second signals. This can be accomplished in a variety of manners. For example, the times that the amplitudes of the received first and second signals cross an amplitude threshold can be determined, in which case, the transit time difference will be a function of the threshold crossing times. If the first and second signals are simultaneously transmitted, the function will be a difference function. That is, the transit time difference will be the difference between the threshold crossing times. As another example, the received first and second signals can be cross-correlated to obtain a time shift between the received first and second signals, in which case, the transit time difference will be a function of the time shift. If the first and second signals are simultaneously transmitted, the function will be an identity function. That is, the transit time difference will be the time shift.

The method further comprises determining a distance difference between the first distance extending from the location element to the first reference element, and a second distance extending from the location element to the second reference element. This distance difference determination is based on the transit time difference. For example, the distance difference may be equal to the product of the transit time difference and the speed of the first and second signals.

The method further comprises determining coordinates of the location element within a coordinate system based on the distance difference. In the preferred method, the first and second reference elements are arranged in an array. In this case, the method may comprise determining an angle between an imaginary line intersecting the location element and the array and a first imaginary plane intersecting the imaginary line. For example, the imaginary line may bisect another imaginary line extending between the first and second reference elements, and the imaginary plane may be perpendicular to other imaginary line. The angle determination will be based on the distance difference and a predetermined distance between the first and second reference elements. The coordinate determination will then be based on the angle and the length of the imaginary line.

When only two reference elements are used, the coordinates of the location element can be determined in a two-dimensional coordinate system. When a third reference element is provided, however, the location element can be determined in a three-dimensional coordinate system. In this case a third signal is wirelessly transmitted between the location element and the third reference element. Another transit time difference of the first and third signals between the location element and the respective first and third reference elements will be determined, and another distance difference between a first distance and a third distance extending from the location element to the third reference element will be determined based on the other transit time difference. The coordinates of the location element will then be determined further based on the other distance difference.

In accordance with a second aspect of the present invention, a medical system is provided. The medical system comprises a medical probe, a location element mounted on the medical probe, and first and second reference elements. In one preferred embodiment, the first and second reference elements are mounted on a rigid structure, e.g., a patch that can be applied to the patient's skin. In one preferred embodiment, the medical probe is a catheter, e.g., an ablation and/or electrophysiology catheter. The location element and first and second reference elements may be acoustic transducers, although other types of transducers are contemplated by the present invention. The medical system further comprises a registration subsystem that is configured for performing the previously described steps in order to determine the positional coordinates of the medical probe within a coordinate system. Optionally, a third reference element can be provided, so that the registration subsystem can determine the positional coordinates of the medical probe within a three-dimensional coordinate system.

In accordance with a third aspect of the present invention, a method of determining a transit time difference between first and second signals is provided. The method comprises wirelessly transmitting the first and second signals (e.g., acoustic signals) between a location element mounted on a medical probe and respective first and second reference elements. The first and second signals may be transmitted in the same manners described above. The method further comprises cross-correlating the received first and second signals to obtain a signal time shift between the received first and second signals. In the preferred method, the first and second signals are cross-correlated by incrementally time shifting the first and second signals relative to each other, multiplying the first and second signals for each time shift, generating a plurality of values as a function of the signal multiplications over time (e.g., integrating the signal multiplications), and identifying a maximum value from the plurality of values. The cross-correlation can also be computed by multiplying in the frequency domain using Fourier transform methods. The signal time shift will be the time shift corresponding to the maximum value. Lastly, the method comprises determining the transit time difference between the first and second signals as a function of the signal time shift. If the first and second signals are simultaneously transmitted, the function will be an identity function. That is, the transit time difference will be the time shift.

In accordance with a fourth aspect of the present invention, a medical system is provided. The medical system comprises a medical probe, a location element mounted on the medical probe, and first and second reference elements. In one preferred embodiment, the first and second reference elements are mounted on a rigid structure, e.g., a patch that can be applied to the patient's skin. In one preferred embodiment, the medical probe is a catheter, e.g., an ablation and/or electrophysiology catheter. The location element and first and second reference elements may be acoustic transducers, although other types of transducers are contemplated by the present invention. The medical system further comprises a processing subsystem that is configured for performing the previously described steps in order to determine the transit time difference between the first and second signals.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
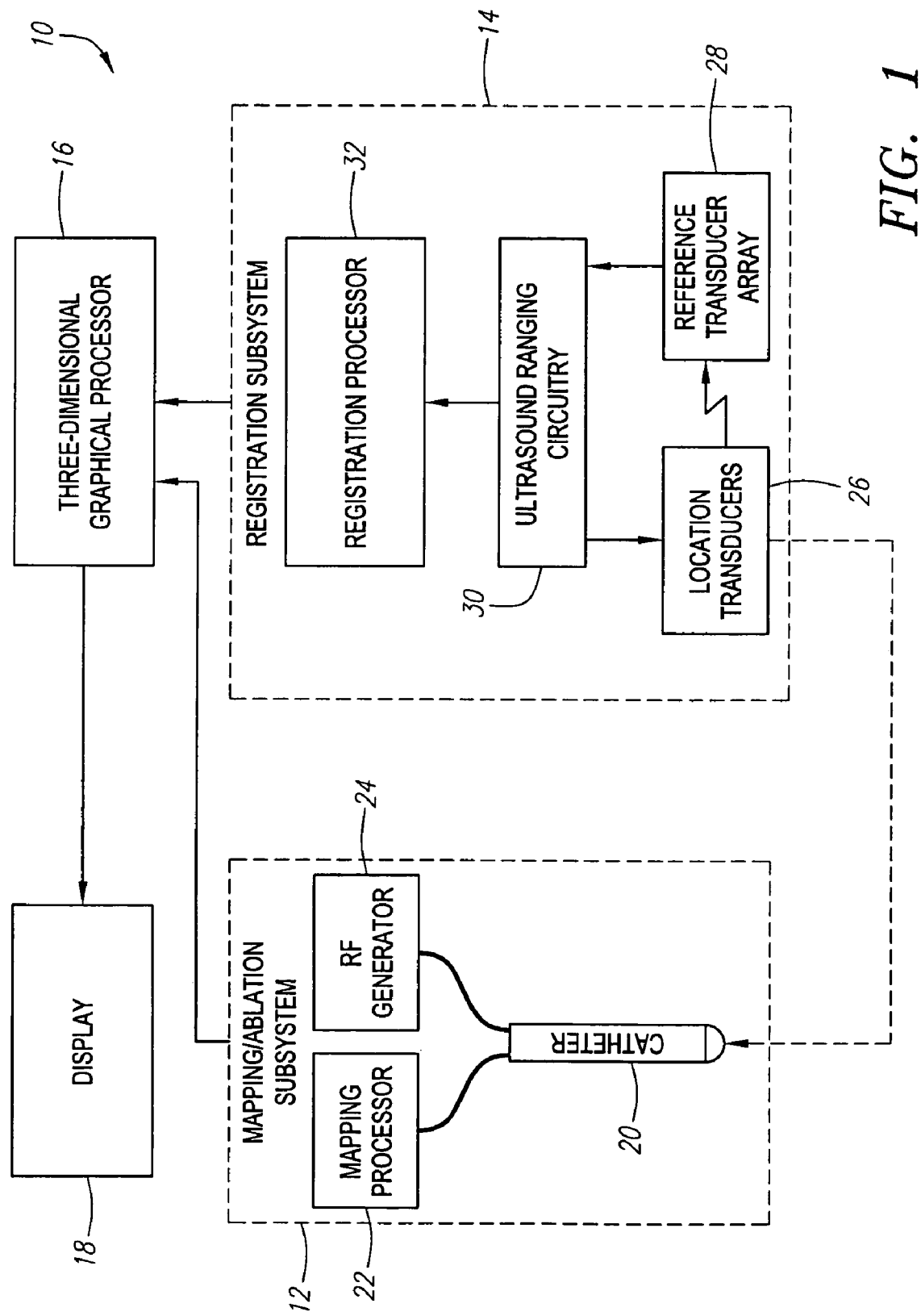
FIG. 1 is a functional block diagram of one preferred embodiment of a medical treatment system constructed in accordance with the present inventions.

Referring to FIG. 1, an exemplary medical treatment system 10 constructed in accordance with the present invention is shown. The treatment system 10 is particularly suited for mapping and treating the heart. Nevertheless, it should be appreciated that it can be used for treating other internal anatomical structures, e.g., the prostrate, brain, gall bladder, uterus, esophagus and other regions in the body. The treatment system 10 generally comprises (1) a mapping/ablation subsystem 12 for mapping and ablating tissue within the heart; (2) a registration subsystem 14 for registering mapping data and the movement of a probe within a three-dimensional graphical environment; (3) a three-dimensional graphical processor 16 for generating three-dimensional graphical data of the environment in which the mapping data is obtained; and (4) a display 18 for displaying the graphical image. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Mapping/Ablation Subsystem

Figure 2:
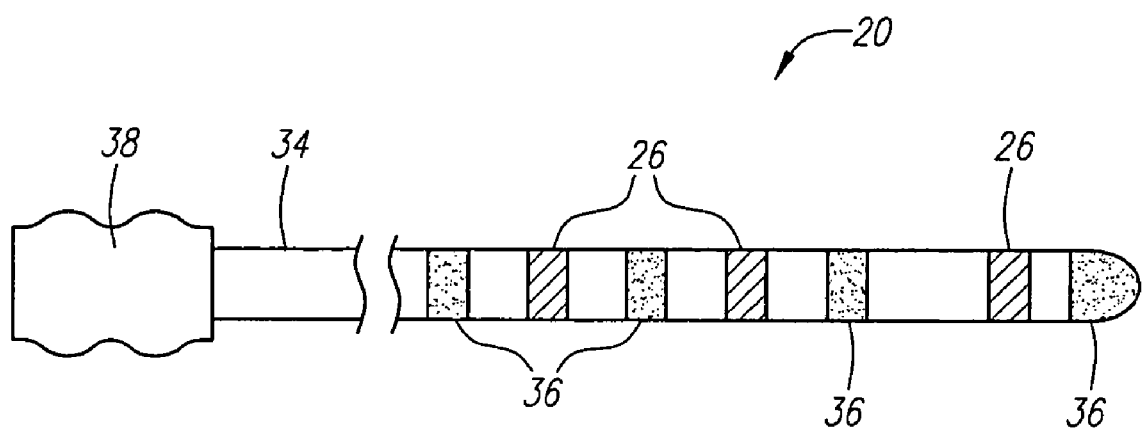
FIG. 2 is a plan view of a mapping/ablation catheter used in the medical treatment system of FIG. 1.

The mapping/ablation subsystem 12 is utilized to identify and treat a target tissue site or sites, e.g., aberrant conductive pathways. To this end, the mapping/ablation subsystem 12 comprises a mapping/ablation catheter 20, a mapping processor 22, and a radio frequency (RF) generator 24. As further illustrated in FIG. 2, the mapping/ablation catheter 20 comprises an elongate catheter member 34, a plurality of electrodes 36 (in this case, four) carried at the distal end of the catheter member 34, and a handle 38 carried at the proximal end of the elongate member 34. All four electrodes 36 on the catheter member 34 are configured to detect electrical signals in the myocardial tissue for subsequent identification of target sites. The electrode 36 at the distal tip of the catheter member 34 is also configured to be used as an ablation electrode to provide ablation energy to the targeted sites when placed adjacent thereto and operated. The handle 38 includes an electrical connector (not shown) for electrical coupling to the mapping processor 22 and RF generator 24.

Referring back to FIG. 1, the mapping processor 22 is configured to derive activation times and voltage distribution from the electrical signals obtained from the electrodes 36 to determine irregular electrical signals within the heart, which can then be graphically displayed as a map. Mapping of tissue within the heart is well known in the art, and thus for purposes of brevity, the mapping processor 22 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 24 is configured to deliver ablation energy to the ablation electrode (i.e., the distal most electrode 36) in a controlled manner in order to ablate sites identified by the mapping processor 22. Alternatively, other types of ablative sources besides the RF generator 24 can be used, e.g., a microwave generator, an acoustic generator, a cryoablation generator, and a laser or other optical generator. Ablation of tissue within the heart is well known in the art, and thus for purposes of brevity, the RF generator 24 will not be described in further detail. Further details regarding RF generators are provided in U.S. Pat. No. 5,383,874, which is expressly incorporated herein by reference.

It should be noted that other types of mapping/ablation catheters can be used in the treatment system 10. For example, a catheter having a basket structure of resilient splines, each of which carries a plurality of dedicated mapping electrodes can be used. This catheter may be placed in a heart chamber, so that the resilient splines conform to the endocardial surface of the heart, thereby placing and distributing the mapping electrodes along the entire endocardial surface of the cavity for efficient mapping. The catheter may also have a roving ablation electrode that can be steered in contact with the ablation sites identified by the mapping electrodes. Or a separate ablation catheter with a dedicated ablation electrode or electrodes can be used.

II. Registration Subsystem Using Thresholding of Signals

Referring back to FIG. 1, the registration subsystem 14 generally comprises (1) a plurality of acoustic transducers, and specifically, acoustic location transducers 26 and an acoustic reference transducer array 28; (2) acoustic ranging circuitry 30 configured for determining the transit times (i.e., the "times-of-flight") for acoustic pulses transmitted between each location transducer 26 and the transducers within the reference transducer array 28; and (3) a registration processor 32 configured for registering the location transducers 26 within a three-dimensional coordinate system based on the transit times provided by the acoustic ranging circuitry 30.

A. Ranging Transducers

Figure 3:
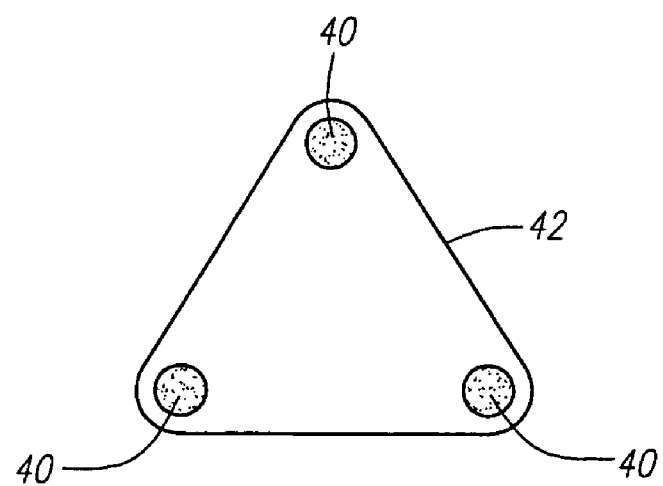
FIG. 3 is a plan view of a reference array used in the medical treatment system of FIG. 1.

As illustrated in FIG. 3, the reference array 28 comprises three acoustic reference transducers 40 and a patch 42 on which the reference transducers 40 are suitably mounted, e.g., using a bonding adhesive. Preferably, the patch 42 is composed of a rigid material, such as stainless steel, so that the respective distances between the reference transducers 40 are fixed and known. Although the reference transducers 40 are arranged in an equilateral triangular configuration, as illustrated in FIG. 3, the reference transducers 40 can be arranged in any configuration as long as the transducers 40 are not arranged in a line, so that a three-dimensional coordinate system can be established. Preferably, the reference array 28 is large enough so that any errors in distance measurements are minimized (e.g., there should be at least a wavelength spacing between the reference transducers 40), as will be described in further detail below, but small enough so that the reference array 28 can be placed in a location on the patient's body that allows all of the reference transducers 40 and location transducers 26 to communicate with each other through a single acoustic window, i.e., without interference from the bones and lungs of the patient. Preferably, the reference transducers 40 are spaced from each other a distance less than 10 mm. As illustrated in FIG. 3, the reference transducers 40 are arranged in a planar configuration in order to simplify calculation of the positional coordinates of the position transducers 26, as will be described in further detail below. It should be noted, however, that the reference transducers 40 can be arranged in a non-planar configuration without straying from the principles taught by the invention—although such an arrangement would require more complex calculations.

The patch 42 may be secured to the patient's skin, such that the transducer array 28 faces the skin. A material, such as a layer of adhesive (not shown), can be substantially permanently affixed or otherwise provided on a surface of the patch 42 to facilitate adhesion of the patch 42 to the skin. The adhesive may be hydrogel, silicon, polyurethane, polyethylene, polypropylene, fluorocarbon polymer, and the like. Alternatively, a separate adhesive may be applied to the patch 42 and/or to the patient's skin before applying the patch 42 in order to secure the transducer array 28 to the patient's skin. Such an adhesive may enhance acoustic coupling of the reference transducers 40 to the patient's skin, and consequently to the location transducers 26. Optionally, additional wetting material, including water, silicone oil, silicone gel, hydrogel, and the like, and/or other acoustically conductive material may be provided between the patch 42 and the patient's skin, e.g., to provide substantial continuity and minimize reflection or other losses and/or to secure the patch 42 to the patient.

The location transducers 26 are mounted at the distal end of a mapping/ablation catheter 20 (shown in FIG. 2), one of which is mounted at the distal tip just proximal to the tip electrode 32, and the remaining two of which are mounted proximally thereto on the distal end. The location transducers 26 facilitate the mapping of electrophysiological information within the heart chamber and the subsequent ablation thereof. As will be described in further detail below, the location transducers 26 also facilitate structural mapping of the endocardial surface of the heart chamber as the mapping/ablation catheter 20 is moved around within the chamber. Optionally, or alternatively, a location transducer 26 can be mounted on the distal tip of a separate marking catheter (not shown) to provide a dedicated means for structurally mapping the heart. Further details on the use of acoustic transducers within the heart for these purposes are described in U.S. Pat. Nos. 6,490,474 and 6,950,689, entitled "A dynamically alterable three-dimensional graphical model of a body region," which are fully and expressly incorporated herein by reference.

As will be described in further detail below, the reference transducers 40 are operated as receive transducers $RX_1$, $RX_2$, and $RX_3$ (shown in FIG. 4), and the positioning transducers 26 are operated as transmit transducers TX (one shown in FIG. 4). It should be noted, however, that, in an alternative embodiment, the reference transducers 40 may be operated as transmit transducers and the location transducers 26 can be operated as receive transducers. The significance is that an acoustic signal is transmitted between a location transducer 26 (whether transmitting or receiving) and a reference transducer 40 (whether receiving or transmitting) to determine the distance therebetween.

It should also be noted that, for purposes of simplicity, each positioning transducer 26 is described as transmitting an acoustic signal that is received by the three reference transducers 40. For the purposes of the invention, however, an acoustic signal is defined as acoustic energy that follows a single path from a transmitting transducer to a receiving transducer. Thus, if an acoustic pulse is transmitted by a single acoustic transducer and received by three different transducers, three acoustic signals have been transmitted. Similarly, if three different transducers transmit acoustic pulses that are received by a single transducer, three acoustic signals have been transmitted.

B. Ranging Circuitry

The acoustic ranging circuitry 30 is configured for conditioning the location transducers 26 as transmitters, i.e., to transmit acoustic signals, and for conditioning the reference transducers 40 as receivers, i.e., to receive acoustic signals. As can be appreciated, acoustic transducers can be operated as transmitters by stimulating them with electrical signals, which in turn causes the transducers to vibrate and transmit acoustic signals. Acoustic transducers can be operated as receivers by receiving electrical signals that are induced by the receipt of acoustic signals and subsequent vibration of the transducers. The acoustic ranging circuitry 30 is configured for determining the distances between each location transducer 26 and the reference transducers 40 by conditioning each location transducer 26 to transmit an acoustic signal, and conditioning the reference transducers 40 to receive that acoustic signal. The acoustic ranging circuitry then measures the transit time for each acoustic pulse. As will be described in further detail below, the registration processor 32 will calculate distances from this time information, which are then used to determine the positional coordinates (x, y, z) of the location transducers 26, and thus any structure or tissue adjacent the location transducers 26, within the three-dimensional coordinate system established by the reference array 28.

Figure 4:
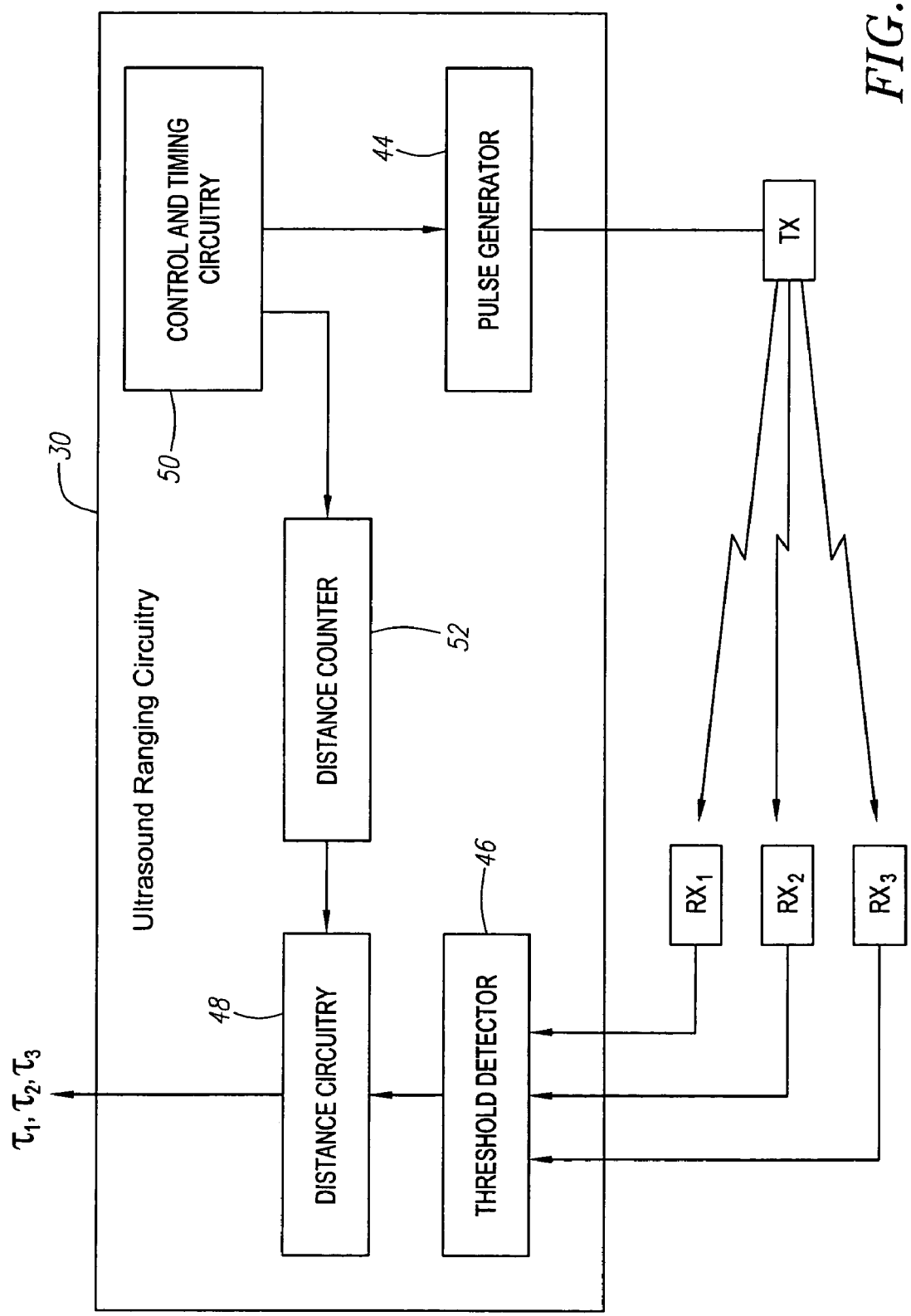
FIG. 4 is a functional block diagram of one preferred implementation of acoustic ranging circuitry used in the medical treatment system of FIG. 1.
Figure 5:
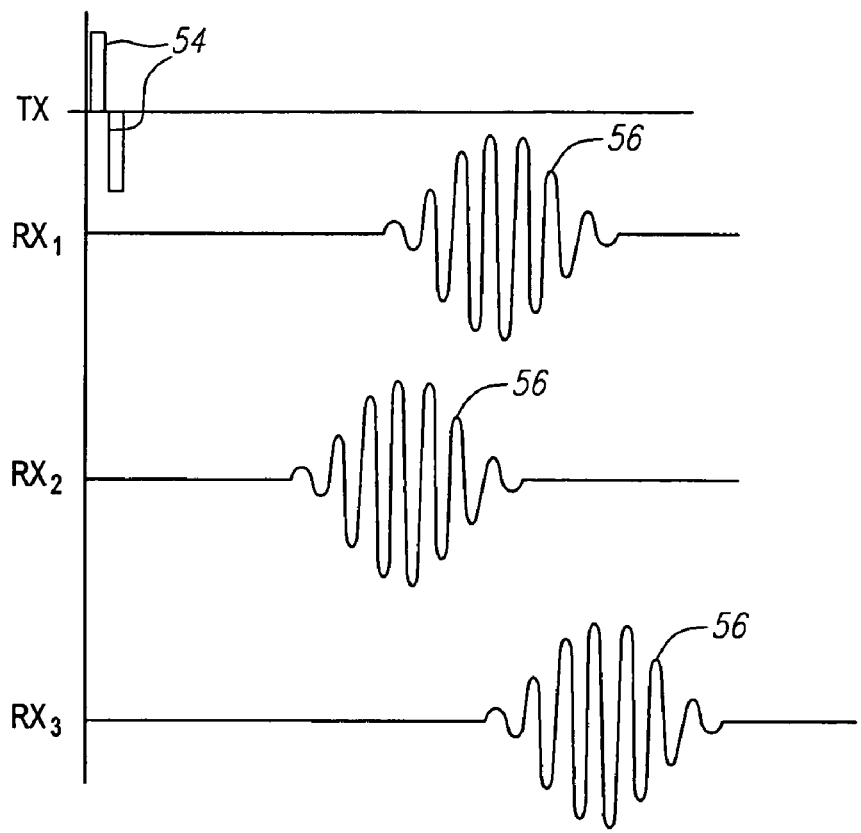
FIG. 5 is a plot of an exemplary electrical signal used to generate an acoustic signal and three resulting electrical signals derived from the receipt of the acoustic signal by three reference transducers used in the reference array of FIG. 3.

Turning now to FIG. 4, the components of the ranging circuitry 30 will now be described in further detail. For purposes of simplicity, the components of the ranging circuitry 30 are described in the context of determining distances between three receive transducers $RX_1$, $RX_2$, and $RX_3$ (e.g., the reference transducers 40) and a single transmit transducer TX, (e.g., one of the location transducers 26). The ranging circuitry 30 includes a pulse generator 44 coupled to the transducer TX, a threshold detector 46 coupled to the transducers $RX_1$, $RX_2$, and $RX_3$, distance circuitry 48 coupled to the threshold detector 46, control and timing circuitry 50 coupled to the pulse generator 44, and a distance counter 52 coupled to the control and timing circuitry 50. With further reference to FIG. 5, the pulse generator 44 is configured for generating an electrical pulse 54 that is transmitted to the transducer TX, which converts the electrical pulse 54 into an acoustic signal that is received by the transducers $RX_1$, $RX_2$, and $RX_3$.

The control and timing circuitry 50 operates the pulse generator 44, such that a series of pulses 54 are generated at the desired frequency and spacing. In the illustrated embodiment, the electrical pulses are single cycle 500 KHz pulses that are transmitted at a rate of one pulse per millisecond. In the practical case where multiple transmitters TX are used, the control and timing circuitry 50 will also control the multiplexing between the pulse generator 44 and the multiple transducers TX, such that the transducers TX are stimulated by the electrical pulses 54 in a sequential fashion. Thus, the control and timing circuitry 50 will cause a first transducer TX to transmit an acoustic pulse 56, then a second transducer TX, and so on until the last transducer TX transmits an acoustic pulse 56. The control and timing circuitry 50 will then cycle through the multiple transmitting transducers TX again.

Coincident with the transmission of each electrical pulse 54, the control and timing circuitry 50 is configured for triggering the distance counter 52 to begin counting from zero. The running count value of the distance counter 52 provides a measure of the transit time of the resulting acoustic signal, i.e., the elapsed time from the transmission of the acoustic signal 56 to the receipt of the acoustic signal. This distance counter 52 is reset to zero upon the transmission of the next electrical pulse 54.

After the acoustic signal has been transmitted, the transducers $RX_1$, $RX_2$, and $RX_3$ receive and convert the acoustic signal into electrical signals 56. The threshold detector 46 is configured for detecting the portion of an electrical signal that is above a threshold level, e.g., a voltage level. The distance circuitry 48 listens for the received electrical signal 56 within a time window, e.g., 100 μsec. The time window may begin immediately or shortly after the electrical pulse 54 has been transmitted. In determining the detection time of the acoustic signal received by a transducer RX, the distance circuitry 48 interprets the first electrical signal that the threshold detector 46 detects within the time window as the received acoustic signal. Upon receipt of each detected electrical signal 56 from the threshold detector 46, the distance circuitry 48 reads the current count from the distance counter 52, which provides a distance measurement between the transducer RX that received the acoustic signal and the transducer TX in the form a transit time.

Thus, it can be appreciated that the ranging circuitry 30 will output a time in the form of a count value for each combination of a transmitting transducer TX and a receive transducer RX. For instance, if there are three transmitting transducers TX and three receive transducers RX, nine count values will be output, each of which represent transit time of an acoustic signal transmitted between the selected pair of transducers TX and RX. It should be noted that only one threshold detector 46, distance circuitry 48, and distance counter 52 are shown for purposes of brevity in illustration. In a practical arrangement, there will be a threshold detector 46 and distance circuitry 48 for each receive transducer RX, since the ranging circuitry 50 must be capable of independently receiving and processing the acoustic signals received by the respective transducers $RX_1$, $RX_2$, and $RX_3$. In this arrangement, a single distance counter 52 can be used, in which case, a latch can be associated with each receive transducer RX in order to capture and hold the counter value when the signal detection occurs.

C. Registration Processor

Referring back to FIG. 1, the registration processor 32 is configured for registering the location transducers 26 within the three-dimensional coordinate system. In performing its registration function, the registration processor 32 first determines the distances between each location transducer 26 and the reference transducers 40 based on the transit times output from the ranging circuitry 30 and a simple distance equation. Once the distances from each location transducer 26 to the three reference transducers 40 are known, the registration processor 32 determines the coordinates of the location transducers 26 within the three-dimensional coordinate system established by the transducer array 28. Specifically, the registration processor 32 determines the coordinates of each location transducer 26 based on a first distance difference between a selected pair of reference transducers 40 and the location transducer 26, and a second distance difference between another selected pair of reference transducers 40 and the location transducer 26.

Figure 6:
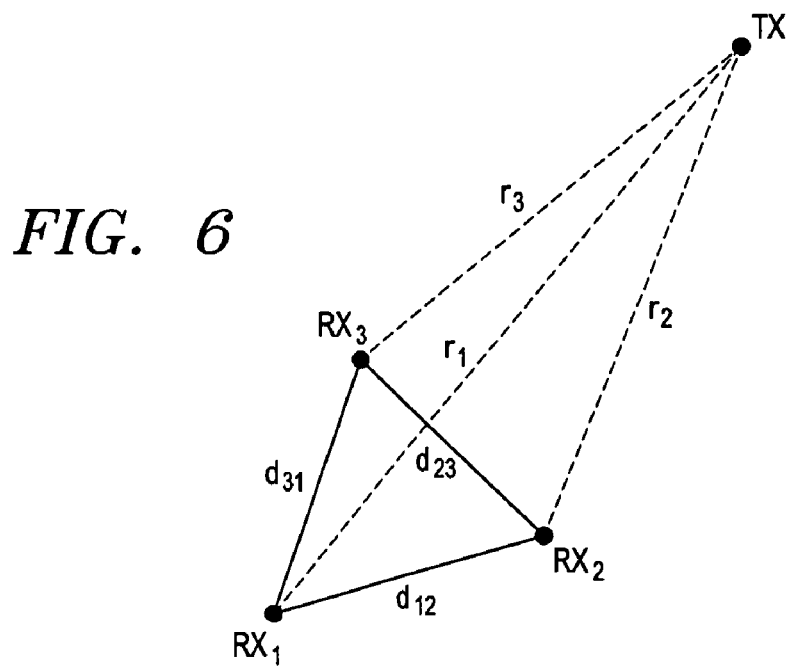
FIG. 6 is a perspective view of three receive transducers that can be used in the reference array of FIG. 3, particularly showing the dimensional arrangement between the transducers.

This procedure will now be described in further detail with reference to FIGS. 6-8. As best shown in FIG. 6, a transmitting transducer TX (e.g., one of the location transducers 26) and three receive transducers $RX_1$, $RX_2$, and $RX_3$ (e.g., the three reference transducers 40) are shown. The receiving transducers $RX_1$, $RX_2$, and $RX_3$ are disposed in a plane of a rigid structure to form a transducer array. The transducer $RX_1$ is separated from the transducer $RX_2$ by a distance $d_{12}$, the transducer $RX_2$ is separated from the transducer $RX_3$ by a distance $d_{23}$, and the transducer $RX_3$ is separated from the transducer $RX_1$ by a distance $d_{31}$. In the illustrated embodiment the distances $d_{12}$, $d_{23}$, and $d_{31}$ are equal. These distances may be different, however, as long as the distances are known by the registration processor 32.

The transducer TX is separated from the respective transducers $RX_1$, $RX_2$, and $RX_3$ by distances $r_1$, $r_2$, and $r_3$. To measure the distances $r_1$, $r_2$, and $r_3$, the equations $r_1 = v\tau_1$, $r_2 = v\tau_2$, and $r_3 = v\tau_3$ can be used, where $v$ is the velocity of acoustic pulses transmitted by the transmitting transducer TX through the medium to the receiving transducers $RX_1$, $RX_2$, and $RX_3$, and $\tau_1$, $\tau_2$, and $\tau_3$ are the transit times for the acoustic signals, i.e., the time that it takes for the acoustic signal to travel between the transducer TX and the respective transducers $RX_1$, $RX_2$, and $RX_3$. To simplify the distance computation, the velocity of the acoustic signals may be assumed to be constant. This assumption typically only produces a small error, since the velocity of acoustic signals (estimated to be 1540 m/s) varies little in soft tissue and blood, assuming that the acoustic signal are transmitted through an acoustic window through soft tissue, i.e., the acoustic signal does not impinge upon bones or air.

Figure 7:
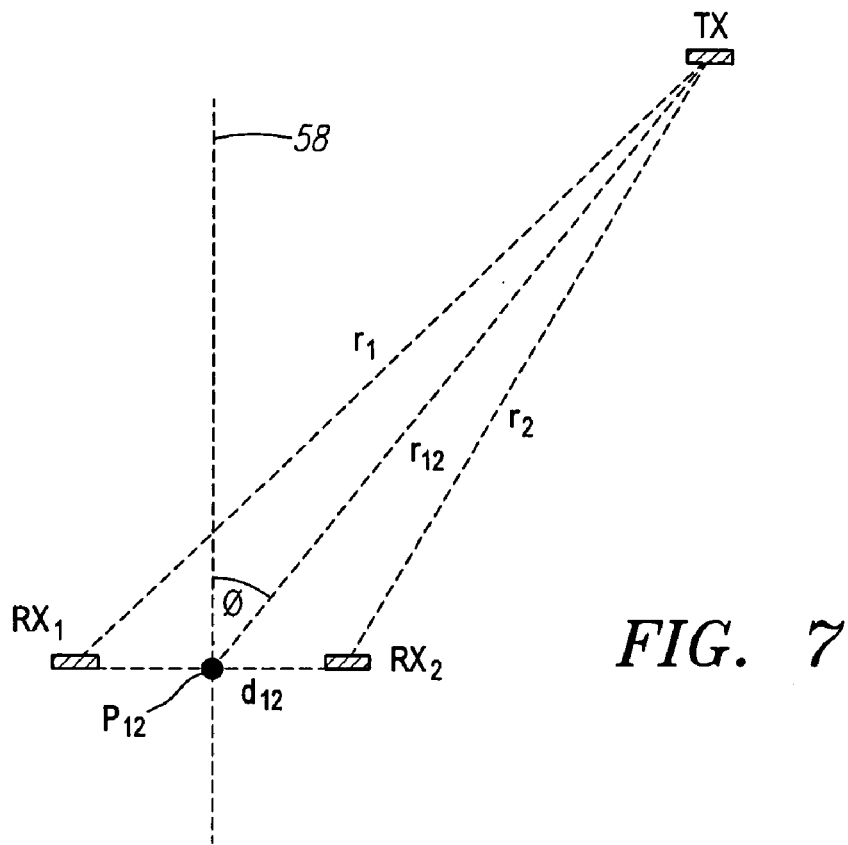
FIG. 7 is a side view of the receive transducers and transmit transducer of FIG. 6.
Figure 8:
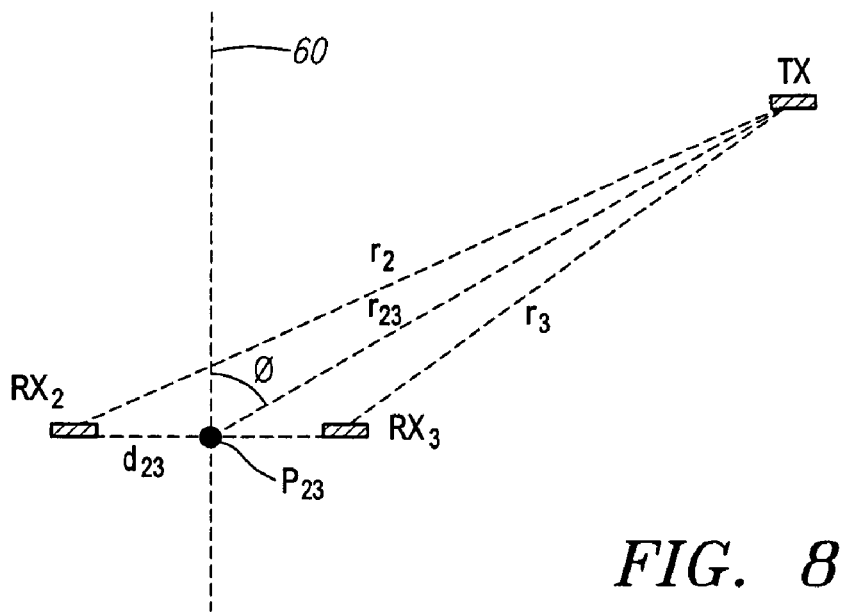
FIG. 8 is another side view of the receive transducers and transmit transducer of FIG. 6.

Referring now to FIGS. 7 and 8, the angles of arrival ($\theta$, $\phi$) of the acoustic signal at two points $p_{12}$ and $p_{23}$ located in the plane of the array are then determined based on distances $r_{12}$ and $r_{23}$ between the transducer TX and the respective points $p_{12}$ and $p_{23}$. The point $p_{12}$ bisects an imaginary line (having a length $d_{12}$) extending between the transducers $RX_1$ and $RX_2$, and the point $p_{12}$ bisects an imaginary line (having a length $d_{23}$) extending between the transducers $RX_2$ and $RX_3$. As illustrated in FIG. 7, the angle $\theta$ is defined between an imaginary line 58, which is perpendicular to the imaginary line $d_{12}$, and an imaginary line (having a length $r_{12}$) extending between the transducer TX and point $p_{12}$. As illustrated in FIG. 8, the angle $\phi$ is likewise defined between an imaginary line 60, which is perpendicular to the imaginary line $d_{23}$, and an imaginary line (having a length $r_{23}$) extending between the transducer TX and point $p_{23}$.

Assuming that $r_{12} \gg d_{12}$ and $r_{23} \gg d_{23}$, then $r_{12} \sim (r_1 + r_2)/2$ and $r_{23} \sim (r_2 + r_3)/2$. Based on basic geometric principles, the difference between the distances $r_1$ and $r_2$ is defined by the equation $dr_{12} = r_1 - r_2 = d_{12} \sin(\theta)$. Thus, the arrival angle $\theta$ can be determined by the equation: $\theta = \sin^{-1}(dr_{12}/d_{12})$. Defining a transit time difference $\Delta\tau_{12} = \tau_1 - \tau_2$, then $\theta = \sin^{-1}(\Delta\tau_{12}v/d_{12})$. Likewise, the difference between the distances $r_2$ and $r_3$ is defined by the equation $dr_{23} = r_2 - r_3 = d_{23} \sin(\phi)$. Thus, the arrival angle $\phi$ can be determined by the equation: $\phi = \sin^{-1}(dr_{23}/d_{23})$. Defining a transit time difference $\Delta\tau_{23} = \tau_2 - \tau_3$, then $\phi = \sin^{-1}(\Delta\tau_{23}v/d_{23})$.

It should be noted that although the distance difference $dr_{12}$ is used to calculate the arrival angle $\theta$, and the distance difference $dr_{23}$ is used to calculate the arrival angle $\phi$, the distance difference $dr_{31}$ can alternatively be used to calculate either of the arrival angles $\theta$ and $\phi$. The significance is that two different combinations of the distances $r_1$, $r_2$, and $r_3$ are used to calculate the respective angles $\theta$ and $\phi$.

Given the arrival angles $\theta$ and $\phi$ and the distances $r_{12}$ and $r_{23}$, the x-y-z positional coordinates of the transducer TX can be calculated as follows, given $r = r_{12} \approx r_{23} \approx r_{31}$, and assuming the receiving transducers $RX_1$, $RX_2$, and $RX_3$ form an equilateral triangle configuration:

$$x = r\sin\theta$$
$$y = r\sqrt{1 - \cos^2\phi - \frac{1}{4}\sin^2\theta}$$
$$z = r\sqrt{\cos^2\phi - \frac{3}{4}\sin^2\theta}$$

The positional coordinates of the remaining location transducers are calculated in the same manner as just described above with respect to the transducer TX.

It should be noted that the orientation of the imaginary lines 58/60 with respect to the imaginary lines between the respective reference transducer pairs are somewhat arbitrary and will not significantly change the manner in which the positional coordinates of the transducer TX is calculated. For example, if the imaginary lines 58/60 are defined as being parallel to the imaginary lines between the respective reference transducer pairs, rather than orthogonal to it, the x-y-z positional coordinates of the transducer TX can, instead, be calculated by the equations:

$$x = r\cos\theta$$
$$y = r\sqrt{1 - \sin^2\phi - \frac{1}{4}\cos^2\theta},$$
$$z = r\sqrt{\sin^2\phi - \frac{3}{4}\cos^2\theta}$$

where $\theta = \cos^{-1}(\Delta\tau_{12}v/d_{12})$ and $\varphi = \cos^{-1}(\Delta\tau_{23}v/d_{23})$.

III. Registration Subsystem Using Correlation

Figure 9:
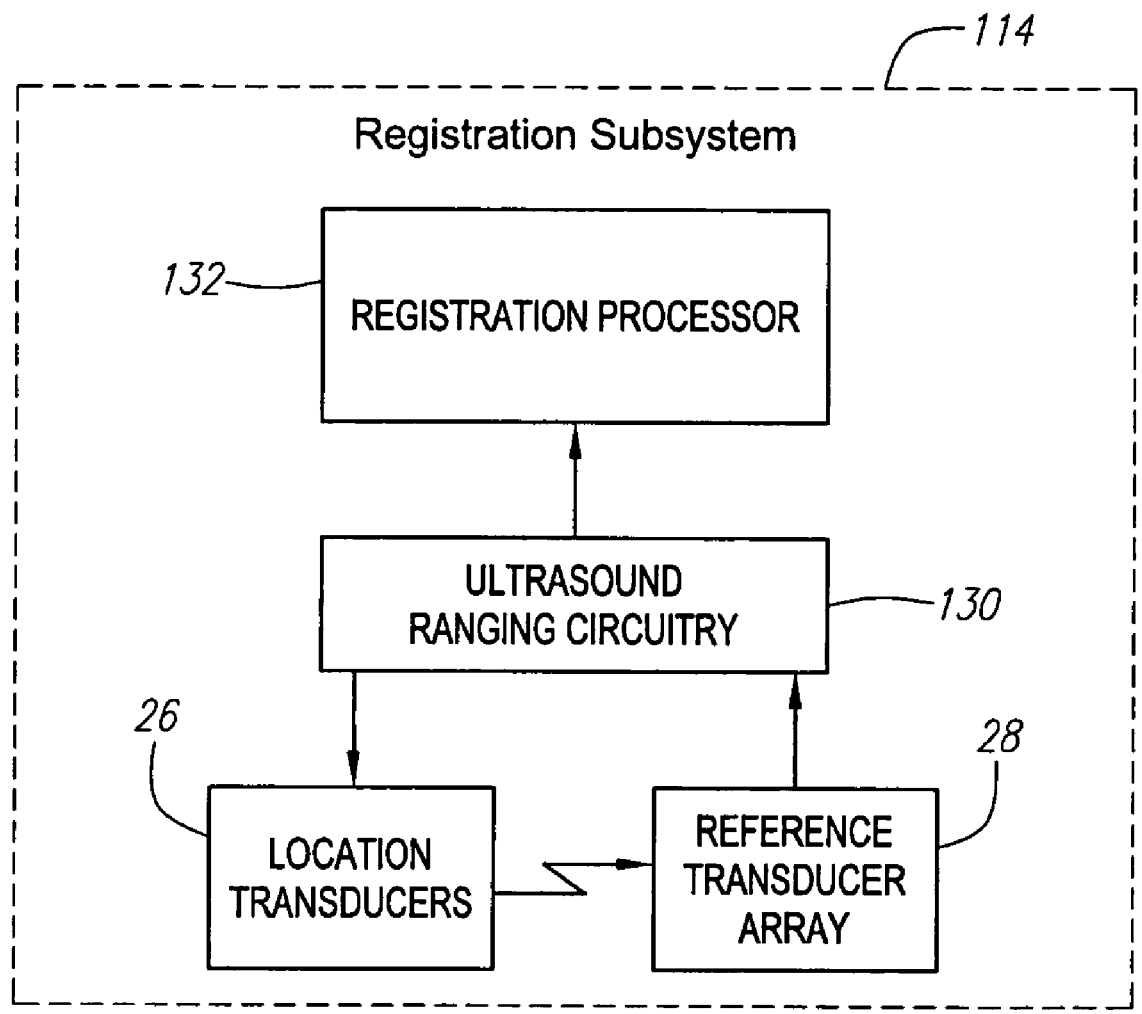
FIG. 9 is an alternative embodiment of a registration subsystem that can be used in the medical treatment system of FIG. 1.

Referring to FIG. 9, an alternative embodiment of a registration subsystem 114 will now be described. The registration subsystem 114 functionally differs in that it determines the transit time difference $\Delta\tau$ between the received acoustic signals by correlating, rather than thresholding, the signals. By analyzing the entire content of the received signals, errors in calculating the distances between the location transducers 26 and the reference array 28 may be reduced.

Specifically, while the threshold detection method is simple to implement in hardware, it may incur distance errors. This is because the signal is actually detected sometime after it is received, i.e., when the amplitude of the received signal passes a threshold. Thus, there is no guarantee that the detection point will be in the first half cycle of the received signal. It can easily be in the second, or in some circumstances, the third half cycle of the received signal. As a result, the detection point in a first signal received by a first transducer may be in the first half cycle of the signal, whereas the detection point in a second signal received by a second transducer may be in the second half cycle of the signal. At a frequency of 500 KHz, each half cycle represents a distance of 1.5 mm, so skipping a half cycle creates a significant error. Even when the detection point is consistently within the first half-cycle of the received signal, there can be significant variations in the detected distance as the amplitude of the signal is varied. Consider in FIG. 7, for example, an arrival angle θ of 90°, a predetermined distance $d_{12}$ between two transducers $RX_1$ and $RX_2$ of 10 mm, and a distance $r_{12}$ between the transducer TX and array of 100 mm. A relatively small error of 1.5 mm in the signal measurement will be "amplified" into an error equal to $\sin^{-1}(1.5/10)*100=15$ mm.

Figure 10:
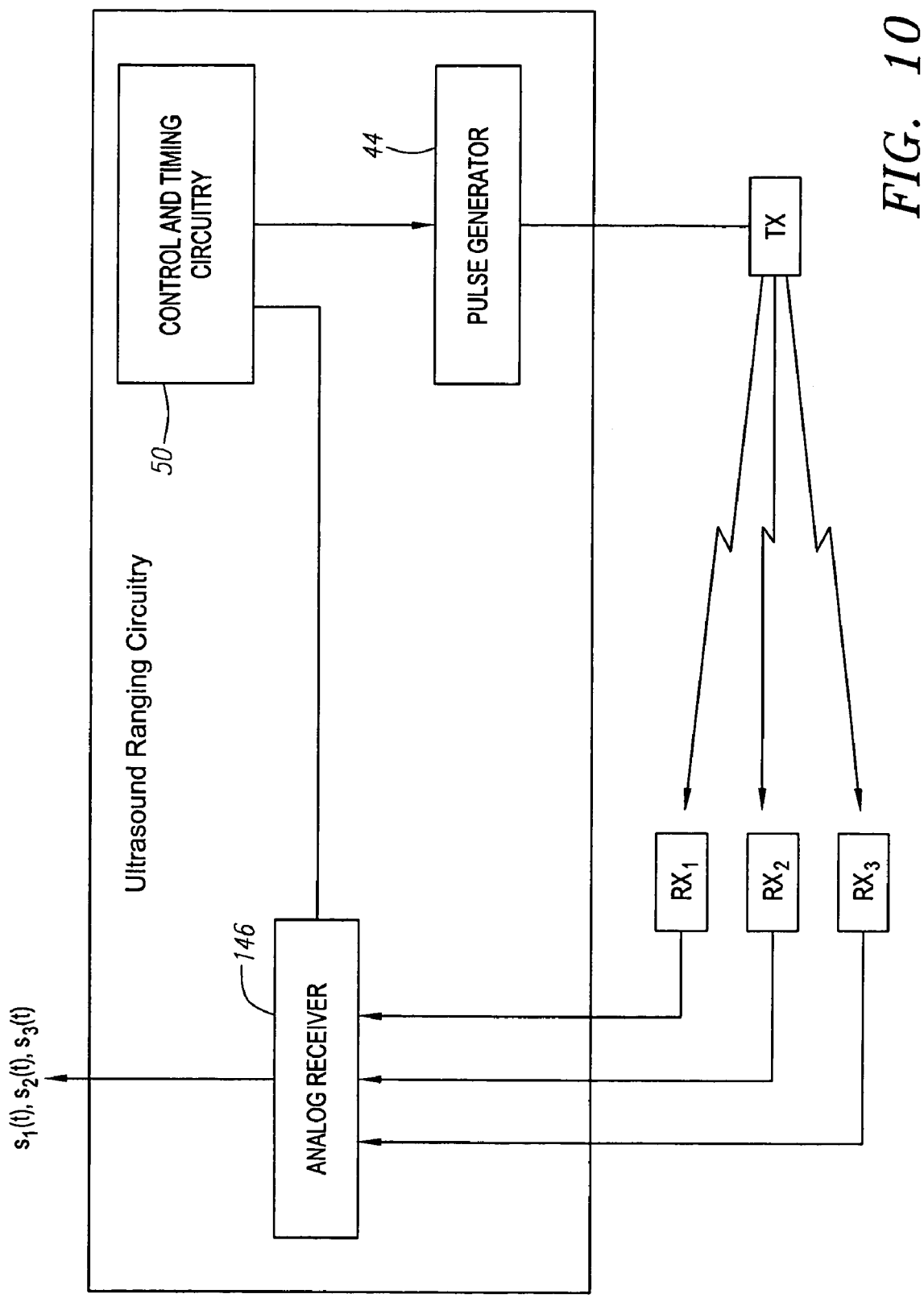
FIG. 10 is a functional block diagram of an alternative embodiment of acoustic ranging circuitry that can be used in the registration subsystem of FIG. 9.

The registration subsystem 114 illustrated in FIG. 9 eliminates, or at least, reduces these distance measurement errors. Specifically, the registration subsystem 114 comprises acoustic ranging circuitry 130, which is similar to the previously described ranging circuitry 30 in that it comprises the pulse generator 44 and control and timing circuitry 50, as illustrated in FIG. 10. Unlike the previously described ranging circuitry 30, the ranging circuitry 130 does not output digital counts representing transit times of signals received by the $RX_1$, $RX_2$, and $RX_3$, but rather outputs the analog signals received by the reference transducers $RX_1$, $RX_2$, and $RX_3$. To this end, the ranging circuitry 130 comprises a receiver 146 that filters and amplifies the signals received from the reference transducers $RX_1$, $RX_2$, and $RX_3$, and then outputs three analog signals $s_1(t)$, $s_2(t)$, and $s_3(t)$ for the respective reference transducers $RX_1$, $RX_2$, and $RX_3$.

The registration subsystem 114 further comprises a registration processor 132 that cross-correlates the analog signals received from the ranging circuitry 130 to obtain the transit time differences $\Delta\tau$ between the signals received by the reference transducers $RX_1$, $RX_2$, and $RX_3$. For example, the registration processor 132 may cross-correlate the analog signals received from transducers $RX_1$ and $RX_2$ to obtain the transit time difference $\Delta\tau_{12}$, and thus the distance difference $dr_{12}$. The registration processor 132 may also cross-correlate the analog signals received from transducers $RX_2$ and $RX_3$ to obtain the transit time difference $\Delta\tau_{23}$, and thus the distance difference $dr_{23}$. The registration processor 132 can then calculate the x-y-z coordinates of the transducer TX using the coordinate transformation equations discussed above.

In the illustrated embodiment, the registration processor 132 determines a transit time difference $\Delta\tau$ by cross-correlating the selected pair of signals and then determining the peak of the cross-correlation as the difference in the time of arrival of the two signals. Specifically, the signals are cross-correlated by iteratively time-shifting the signals relative to each other, multiplying the time-shifted signals, and then integrating the products to obtain the time-shift that results in the maximum cross-correlated energy. The cross-correlation can be calculated as: $R(\tau)=\int s_1(t)s_2(t-\tau)dt$, where $s_1(t)$ is the first received signal as a function of time t, $s_2(t)$ is the second received signal as a function of time t. The transit time difference is the maximum of the cross-correlation.

This correlation procedure is significantly more accurate than the previously described thresholding procedure, since it the entire signal, rather than the detection times, of the signals that are analyzed. In addition, higher frequency modes of the transducers can be used to achieve higher temporal resolution. In fact, it is desirable to operate the registration subsystem 114 with as wide of a frequency band as possible.

Figure 11:
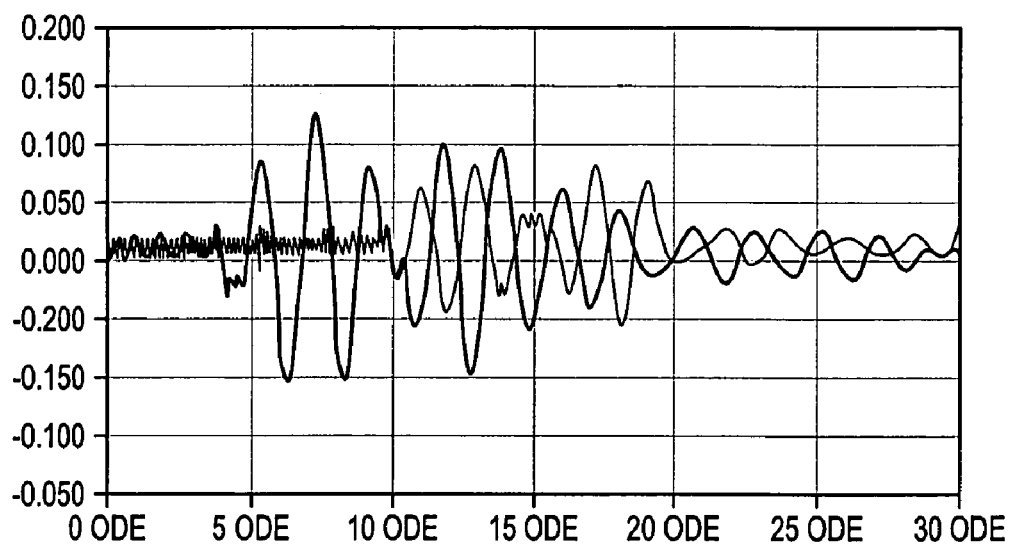
FIG. 11 is a plot of two experimental electrical signals output from a reference transducer array in response to receiving an acoustic signal transmitted from a location transducer.

Referring now to FIG. 11-14, the results of an experimental correlation procedure used to determine the transit time difference $\Delta\tau$ between signals $s_1(t)$ and $s_2(t)$ are shown. In performing the experiment, a single acoustic transducer was used to transmit an acoustic signal to a sensor array. The sensor array contained two acoustic transducers, which were connected to an analog receiver that output the resulting signals $s_1(t)$ and $s_2(t)$. A National Instruments 9112 digital oscilloscope card having a sampling rate of 100 MHz was used to record the signals $s_1(t)$ and $s_2(t)$, which are illustrated in FIG. 11. As can be seen, the amplitude of the first signal $s_1(t)$ is generally greater than the amplitude of the second signal $s_2(t)$. This is due to the different characteristics between transducers. Such variance in amplitude between the signals, however, does not adversely affect the results, since it is the cross-correlation of the signals $s_1(t)$ and $s_2(t)$ that dictates the results.

Figure 12:
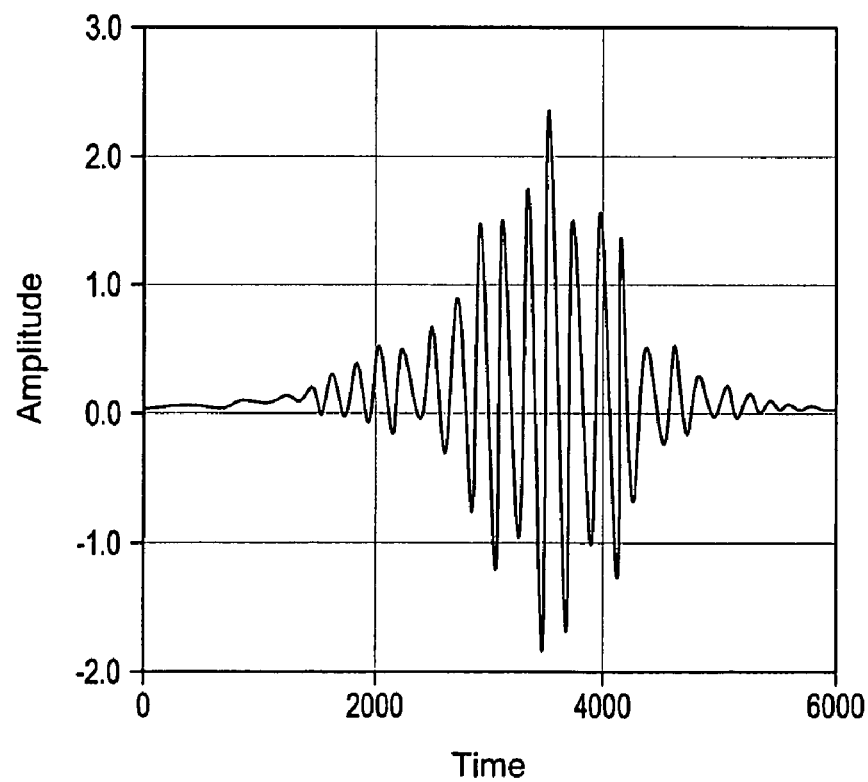
FIG. 12 is a plot of the cross-correlation energy of the electrical signals of FIG. 11 as a function of time shift.
Figure 13:
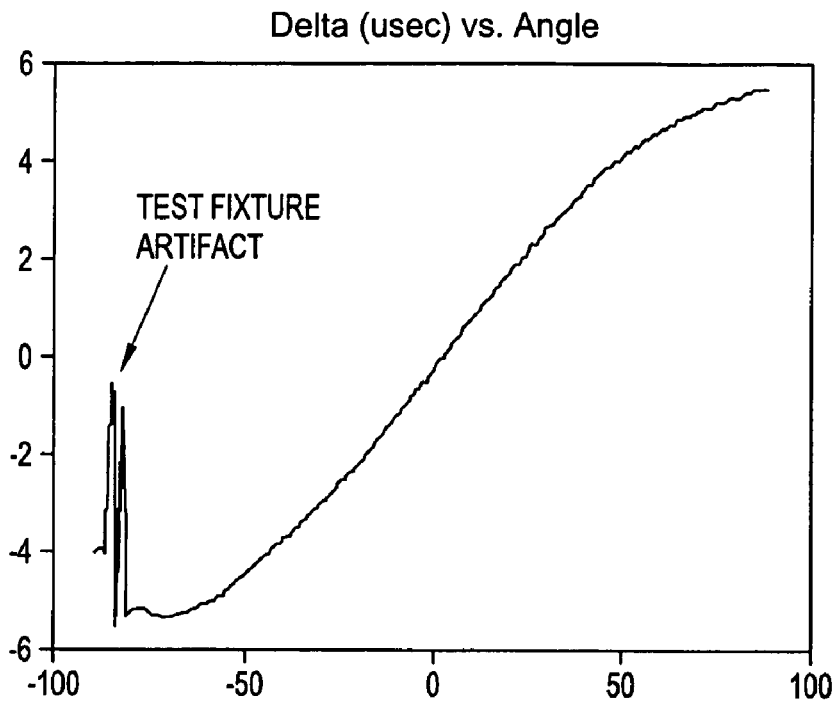
FIG. 13 is a plot of a transit time difference of the electrical signal of FIG. 11 as a function of the angle between the transducer array and the location transducer.
Figure 14:
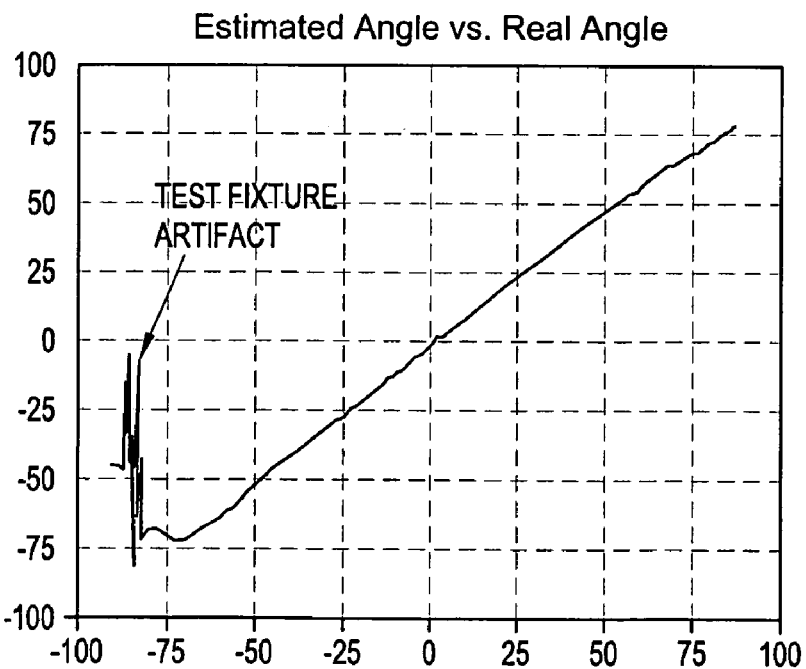
FIG. 14 is a plot of the calculated angle between the transducer array and the location transducer as a function of the actual angle between the transducer array and the location transducer.

A labview program was used to perform a cross-correlation of the signals $s_1(t)$ and $s_2(t)$, while physically changing the angle of the sensor array relative to the transmitting transducer. FIG. 12 illustrates the cross-correlation. As can be seen, the peak occurs around 3.5 msec. Thus, in this case, the transit time difference $\Delta\tau$ of the acoustic signals received by the two receive transducers is approximately 3.5 msec. FIG. 13 illustrates the transit time difference $\Delta\tau$ as a function of the angle of the sensor array relative to the transmitting transducer. As predicted, there is a sinusoidal shape to the transit time difference $\Delta\tau$. Notably, the artifact near −90 degrees is caused by the acoustic shadowing of the fixture that holds the transmitting transducer. Thus, in a practical environment, no such artifact will appear in the measurement. FIG. 14 illustrates the calculated estimated angle of the sensor array relative to the transmitting transducer versus the actual angle of the sensor array. As can be seen, the estimated angle tracks the actual angle fairly closely in the range of −50 to 50 degrees, and tapers off somewhat outside of this range. Much of the angle error outside of the −50 to 50 degree range can be attributed to the fact that the distance between the reference transducers was measured by hand. In a practical scenario, the distances between reference transducers can be more tightly controlled in order to minimize measurement errors. Again, the artifact near −90 degrees is caused by the acoustic shadowing of the fixture that holds the transmitting transducer.

IV. Three-Dimensional Rendering Processor

The three-dimensional graphical processor 16 is configured for generating a global representation of an internal anatomical structure in the form of a computer-generated representation (i.e., a reconstruction) of the heart chamber within the global coordinate system. The three-dimensional graphical processor 16 accomplishes this by acquiring the positions of the location transducers 26 within the global coordinate system as the mapping/ablation catheter 20 is moved around within the cavity of the internal anatomical structure, and then deforming an anatomical shell to the acquiring positions. The three-dimensional graphical processor 16 is also configured to construct a graphical representation of the mapping/ablation catheter 20 within the graphical representation of the internal anatomical structure based on the calculated positional coordinates of the location transducers 26 located at the distal end of the catheter 20 and the known positional relationship between the location transducers.

The three-dimensional graphical processor 16 is also configured for superimposing an electrical activity map over the graphical representation of the internal anatomical structure based on the electrical activity information acquired from the mapping/ablation subsystem 12 and the positions of the mapping electrodes 36 geometrically derived from the positions of the location transducers 26 obtained from the registration subsystem 16. This electrical activity map illustrates sites of interest, e.g., electrophysiology recording and ablation sites, for providing subsequent ablative treatment. Additional details on this graphical reconstruction technique can be found in U.S. Pat. Nos. 6,490,474 and 6,950,689, entitled "A dynamically alterable three-dimensional graphical mode of a body region," which are expressly incorporated herein by reference.

Instead of, or in addition to, graphically reconstructing the body tissue, any one of a number of imaging techniques to generate a three-dimensional image of the body tissue. For example, a Magnetic Resonance Imaging (MRI) imager, or a Computed Tomography (CT) imager can be used to generate a three-dimensional image of the internal anatomical structure. To accomplish this, the imager may be moved laterally and/or rotationally to obtain multiple cross-sectional or sector images of the body tissue at different positions within the body tissue. The multiple cross-sectional images may then be aggregated (i.e., pieced together) to reconstruct a three-dimensional image of the internal anatomical structure. The three-dimensional image of the internal anatomical structure may be registered within the global coordinate system by tracking the position of the imager, and therefore the cross-sectional or sector images taken by the imager, for example, by attaching acoustic location transducers to the imager. Alternatively, the position of anatomic landmarks within the body tissue may be determined in the global coordinate system, e.g., using the mapping/ablation catheter 20. The three-dimensional image of the internal anatomical structure may then be registered with the global coordinate system by correlating the positions of the anatomic landmarks in the three-dimensional image of the internal anatomical structure with the determined positions of the anatomic landmarks in the global coordinate system.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of determining the location of a medical probe, comprising:
   wirelessly transmitting first and second signals between a location element mounted on the medical probe and first and second reference elements;
   determining a transit time difference between the first and second signals;
   determining a distance difference between a first distance extending from the location element to the first reference element and a second distance extending from the location element to the second reference element, based on the transit time difference; and
   determining coordinates of the location element within a coordinate system based on the distance difference.

2. The method of claim 1, wherein the first and second signals are acoustic signals.

3. The method of claim 1, wherein the first and second signals are simultaneously transmitted.

4. The method of claim 1, further comprising receiving the first and second signals, and determining times that the amplitudes of the received first and second signals cross an amplitude threshold, wherein the transit time difference is a function of the threshold crossing times.

5. The method of claim 4, wherein the first and second signals are simultaneously transmitted, and the function is a difference function.

6. The method of claim 1, further comprising receiving the first and second signals, and cross-correlating the received first and second signals to obtain a time shift between the received first and second signals, wherein the transit time difference is a function of the time shift.

7. The method of claim 6, wherein the first and second signals are simultaneously transmitted, and the function is an identity function.

8. The method of claim 1, wherein the first and second reference elements are arranged in an array, the method further comprising determining an angle between an imaginary line intersecting the location element and the array and a first imaginary plane intersecting the imaginary line, wherein the angle determination is based on the distance difference and a predetermined distance between the first and second reference elements, and the coordinate determination is based on the angle.

9. The method of claim 8, wherein the coordinate determination is further based on the length of the imaginary line.

10. The method of claim 8, wherein the imaginary plane is perpendicular to another imaginary line extending between the first and second reference elements.

11. The method of claim 8, wherein the imaginary line bisects another imaginary line extending between the first and second reference elements.

12. The method of claim 1, wherein the first and second reference elements are located exterior to a patient's body when the first and second signals are transmitted.

13. The method of claim 1, wherein the coordinate system is a two-dimensional coordinate system.

14. The method of claim 1, further comprising:
   wirelessly transmitting a third signal between the location element and a third reference element;
   determining another transit time difference between the first and third signals;
   determining another distance difference between the first distance and a third distance extending from the location element to the third reference element based on the other transit time difference; and
   determining coordinates of the location element within a coordinate system based further on the other distance difference.

15. The method of claim 14, wherein the coordinate system is a three-dimensional coordinate system.

16. A medical system, comprising:
   a medical probe;
   a location element mounted on the medical probe;
   first and second reference elements; and
   a registration subsystem configured for wirelessly transmitting first and second signals between the location element and the first and second reference elements, determining a transit time difference of the first and second signals between the location element and the respective first and second reference elements, determining a distance difference between a first distance extending from the location element to the first reference element and a second distance extending from the location element to the second reference element, based on the transit time difference; and determining coordinates of the location element within a coordinate system based on the distance difference.

17. The system of claim 16, wherein the location element and first and second reference elements comprise acoustic transducers.

18. The system of claim 16, wherein the registration subsystem is configured for simultaneously transmitting the first and second signals.

19. The system of claim 16, wherein the registration subsystem is configured for receiving the first and second signals, and determining times that the amplitudes of the received first and second signals cross an amplitude threshold, wherein the transit time difference is a function of the threshold crossing times.

20. The system of claim 19, wherein the registration subsystem is configured for simultaneously transmitting the first and second signals, and the function is a difference function.

21. The system of claim 16, wherein the registration subsystem is configured for receiving the first and second signals, and cross-correlating the received first and second signals to obtain a time shift between the received first and second signals, wherein the transit time difference is a function of the time shift.

22. The system of claim 21, wherein the registration subsystem is configured for simultaneously transmitting the first and second signals, and the function is an identity function.

23. The system of claim 16, further comprising a rigid structure on which the first and second reference element are arranged in an array, wherein the registration subsystem is configured for determining an angle between an imaginary line intersecting the location element and the array and a first imaginary plane intersecting the imaginary line, wherein the angle determination is based on the distance difference and a predetermined distance between the first and second reference elements, and the coordinate determination is based on the angle.

24. The system of claim 23, wherein the coordinate determination is further based on the length of the imaginary line.

25. The system of claim 23, wherein the imaginary plane is perpendicular to another imaginary line extending between the first and second reference elements.

26. The system of claim 23, wherein the imaginary line bisects another imaginary line extending between the first and second reference elements.

27. The system of claim 16, wherein the coordinate system is a two-dimensional coordinate system.

28. The system of claim 16, wherein the rigid structure is a patch configured to be located on the skin of a patient.

29. The system of claim 16, further comprising a third reference element, wherein the registration subsystem is further configured for wirelessly transmitting a third signal between the location element and the third reference element, determining another transit time difference of the first and third signals between the location element and the respective first and third reference elements, determining another distance difference between the first distance and a third distance extending from the location element to the third reference element based on the other transit time difference, and determining coordinates of the location element within a coordinate system based further on the other distance difference.

30. The system of claim 29, wherein the coordinate system is a three-dimensional coordinate system.

31. The system of claim 16, wherein the medical probe is a catheter.

32. The system of claim 16, wherein the medical probe is an ablation catheter.

33. The system of claim 16, wherein the medical probe is an electrophysiology mapping catheter.

34. A method of determining the location of a medical probe using an array of reference elements, comprising:
wirelessly transmitting first and second signals between a location element mounted on the medical probe and first and second reference elements located within the reference array;
determining a transit time difference between the first and second signals;
determining a distance difference between a first distance extending from the location element to the first reference element and a second distance extending from the location element to the second reference element, based on the transit time difference;
determining an angle formed by the location element and the reference array based on the distance difference and a distance between the first and second reference elements; and
determining coordinates of the location element within a coordinate system based on the angle.

35. The method of claim 34, wherein the first and second signals are acoustic signals.

36. The method of claim 34, wherein the first and second signals are simultaneously transmitted.

37. The method of claim 34, wherein the coordinate system is a two-dimensional coordinate system.

38. The method of claim 34, wherein the coordinates of the location element are determined based further on a distance between the location element and the reference array.

39. The method of claim 34, wherein the first and second reference elements are located exterior to a patient's body when the first and second signals are transmitted.

40. The method of claim 34, further comprising:
wirelessly transmitting a third signal between the location element and a third reference element located within the reference array;
determining another transit time difference between the first and third signals;
determining another distance difference between the first distance and a third distance extending from the location element to the third reference element based on the other transit time difference;
determining another angle formed by the location element and the reference array based on the distance difference and a distance between the first and third reference elements; and
determining coordinates of the location element within the coordinate system further based on the other angle.

41. The method of claim 40, wherein the coordinate system is a three-dimensional coordinate system.

42. A medical system, comprising:
a medical probe;
a location element mounted on the medical probe;

a reference array having a rigid structure and first and second reference elements mounted on the rigid structure; and a registration subsystem configured for wirelessly transmitting first and second signals between the location element and the first and second reference elements, determining a transit time difference between the first and second signals, determining a distance difference between a first distance extending from the location element to the first reference element and a second distance extending from the location element to the second reference element, based on the transit time difference, determining an angle formed by the location element and the reference array based on the distance difference and a distance between the first and second reference elements, and determining coordinates of the location element within a coordinate system based on the angle.

43. The system of claim 42, wherein the location element and first and second reference elements comprise acoustic transducers.

44. The system of claim 42, wherein the registration subsystem is configured for simultaneously transmitting the first and second signals.

45. The system of claim 42, wherein the coordinate system is a two-dimensional coordinate system.

46. The system of claim 42, wherein the rigid structure is a patch configured to be located on the skin of a patient.

47. The system of claim 42, wherein the registration subsystem is configured to determine the coordinates of the location element based further on a distance between the location element and the reference array.

48. The system of claim 42, wherein the reference array has a third reference element mounted on the rigid structure, and wherein the registration subsystem is further configured for wirelessly transmitting a third signal between the location element and the third reference element, determining another transit time difference between the first and third signals, determining another distance difference between the first distance and a third distance extending from the location element to the third reference element based on the other transit time difference, determining another angle formed by the location element and the reference array based on the distance difference and a distance between the first and third reference elements, and determining coordinates of the location element within the coordinate system further based on the other angle.

49. The system of claim 48, wherein the coordinate system is a three-dimensional coordinate system.

50. The system of claim 42, wherein the medical probe is a catheter.

51. The system of claim 42, wherein the medical probe is an ablation catheter.

52. The system of claim 42, wherein the medical probe is an electrophysiology mapping catheter.

53. A method of determining a transit time difference between first and second signals, comprising:

wirelessly transmitting the first and second signals between a location element mounted on a medical probe and respective first and second reference elements;

receiving the first and second signals;

cross-correlating the received first and second signals to obtain a signal time shift between the received first and second signals; and determining the transit time difference as a function of the signal time shift.

54. The method of claim 53, wherein the first and second signals are acoustic signals.

55. The method of claim 53, wherein the first and second signals are simultaneously transmitted.

56. The method of claim 55, wherein the function is an identity function.

57. The method of claim 53, wherein the first and second signals are cross-correlated by:

incrementally time shifting the first and second signals relative to each other;

multiplying the first and second signals for each time shift;

generating a plurality of values as a function of the signal multiplications over time;

identifying a maximum value from the plurality of values, wherein the signal time shift is the time shift corresponding to the maximum value.

58. The method of claim 57, wherein the function is an integration function.

59. A medical system, comprising:

a medical probe;

a location element mounted on the medical probe;

first and second reference elements; and processing circuitry configured for wirelessly transmitting first and second signals between the location element and the respective first and second reference elements, receiving the first and second signals, cross-correlating the received first and second signals to obtain a signal time shift between the received first and second signals, and determining a transit time difference between the first and second signals as a function of the signal time shift.

60. The system of claim 59, wherein the location element and first and second reference elements comprise acoustic transducers.

61. The system of claim 59, wherein the registration subsystem is configured for simultaneously transmitting the first and second signals.

62. The system of claim 59, wherein the function is an identity function.

63. The system of claim 59, wherein the processing circuitry cross-correlates the first and second signals by:

incrementally time shifting the first and second signals relative to each other;

multiplying the first and second signals for each time shift;

generating a plurality of values as a function of the signal multiplications over time;

identifying a maximum value from the plurality of values, wherein the signal time shift is the time shift corresponding to the maximum value.

64. The system of claim 63, wherein the function is an integration function.

65. The system of claim 59, wherein the medical probe is a catheter.

66. The system of claim 59, wherein the medical probe is an ablation catheter.

67. The system of claim 59, wherein the medical probe is an electrophysiology mapping catheter.

* * * * *